US010363159B1

(12) United States Patent
LoGuercio

(10) Patent No.: US 10,363,159 B1
(45) Date of Patent: Jul. 30, 2019

(54) PAIN MANAGEMENT AND POST-OPERATIVE HIP ORTHOSIS

(71) Applicant: Outcome-Based Technologies LLC, Cheyenne, WY (US)

(72) Inventor: Donald P. LoGuercio, Scottsdale, AZ (US)

(*) Notice: Subject to any disclaimer, the term of this patent is extended or adjusted under 35 U.S.C. 154(b) by 0 days.

(21) Appl. No.: 16/112,631

(22) Filed: Aug. 24, 2018

(51) Int. Cl.
*A61F 5/01* (2006.01)
*A61F 7/00* (2006.01)

(52) U.S. Cl.
CPC .......... *A61F 5/0193* (2013.01); *A61F 5/0102* (2013.01); *A61F 5/0104* (2013.01); *A61F 7/0085* (2013.01); *A61F 2005/0172* (2013.01); *A61F 2007/004* (2013.01); *A61F 2007/0056* (2013.01)

(58) Field of Classification Search
CPC .. A61F 5/0193; A61F 5/30; A61F 2005/0183; A61F 5/24; A61F 5/028; A61F 5/0102; A61F 5/0104; A61F 2007/0228; A61F 2007/023; A61F 2007/0001; A61F 7/10; A61F 2007/0231; A61F 2007/0024; A61F 2007/0039; A61F 5/05; A61F 2007/0025; A61F 2007/0026; A61F 2007/0027; A61F 5/34; A61F 5/37; A61F 5/024; A61F 5/026; A61F 5/0009; A61F 5/3776; A61F 5/3784; A61F 13/145; A61F 2013/004; A61F 2013/00553; A61F 5/05841; A61F 5/40; A61F 5/26; A61F 13/64; A61F 13/06; A61F 2013/00174; A61F 5/28; A61F 2005/0182

See application file for complete search history.

(56) References Cited

U.S. PATENT DOCUMENTS

| | | | |
|---|---|---|---|
| 5,514,155 A * | 5/1996 | Daneshvar ......... | A61B 17/1325 128/118.1 |
| 2010/0152823 A1* | 6/2010 | Muchowicz .............. | A61F 7/10 607/112 |
| 2017/0055687 A1* | 3/2017 | Diaz ...................... | A45F 5/021 |

* cited by examiner

Primary Examiner — Ophelia A Hawthorne
(74) Attorney, Agent, or Firm — Thomas W. Galvani, P.C.; Thomas W. Galvani

(57) ABSTRACT

An improved pain management and post-operative hip orthosis includes a waist strap having first and second ends and a lateral portion therebetween, a lower strap having first and second ends and a lateral portion therebetween, and a pocket extending between the waist strap and lower strap. The pocket has inner and outer panel fastened to each other to define an upper opening and a lower opening. The orthosis further includes an abduction harness including two upper straps and a lower strap coupled to each other at a central union, wherein the upper straps are secured to the top of the pocket and the lower strap is secured to the bottom of the pocket. The orthosis still further includes a rotation strap extending from the bottom of the pocket to a location on the waist strap proximate to the top of the pocket.

21 Claims, 12 Drawing Sheets

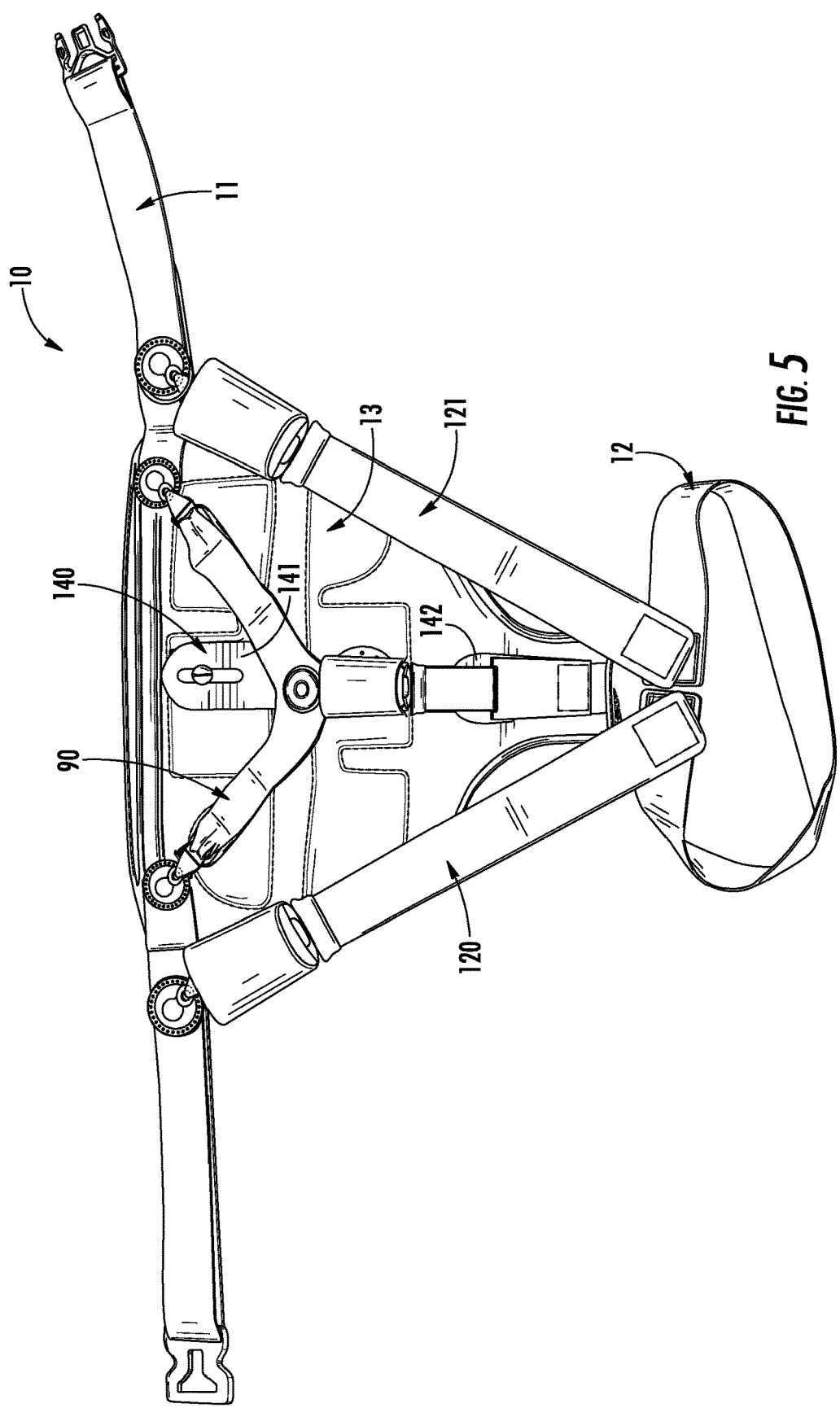

PAIN MANAGEMENT AND POST-OPERATIVE HIP ORTHOSIS

FIELD OF THE INVENTION

The present invention relates generally to medical devices, and more particularly to devices used for post-operative care and pain management.

BACKGROUND OF THE INVENTION

There are many types of post-operative orthotic devices from which doctors and patients may choose. Likewise, there are many types of pain management devices available to aid recovery after surgery. All devices have particular features and drawbacks. Improved devices are always needed, to enable or limit movement in certain directions, to control temperature at a surgical site, to apply or remove pressure on a body part, to rotate, abduct, or adduct a limb, to support or add weight, to stabilize joints, and for various other reasons.

SUMMARY OF THE INVENTION

An improved pain management and post-operative hip orthosis includes a waist strap having first and second ends and a lateral portion therebetween, a lower strap having first and second ends and a lateral portion therebetween, and a pocket extending between the waist strap and lower strap. The pocket has inner and outer panel fastened to each other to define an upper opening and a lower opening. The orthosis further includes an abduction harness including two upper straps and a lower strap coupled to each other at a central union, wherein the upper straps are secured to the top of the pocket and the lower strap is secured to the bottom of the pocket. The orthosis still further includes a rotation strap extending from the bottom of the pocket to a location on the waist strap proximate to the top of the pocket.

The above provides the reader with a very brief summary of some embodiments discussed below. Simplifications and omissions are made, and the summary is not intended to limit or define in any way the scope of the invention or key aspects thereof. Rather, this brief summary merely introduces the reader to some aspects of the invention in preparation for the detailed description that follows.

BRIEF DESCRIPTION OF THE DRAWINGS

Referring to the drawings:

FIGS. 3-5 are elevation views of the orthosis of FIG. 1 in stages of application with various elements, including an abduction harness in FIG. 3, rotation straps in FIG. 4, and an articulating brace in FIG. 5;

DETAILED DESCRIPTION

Figure 1:
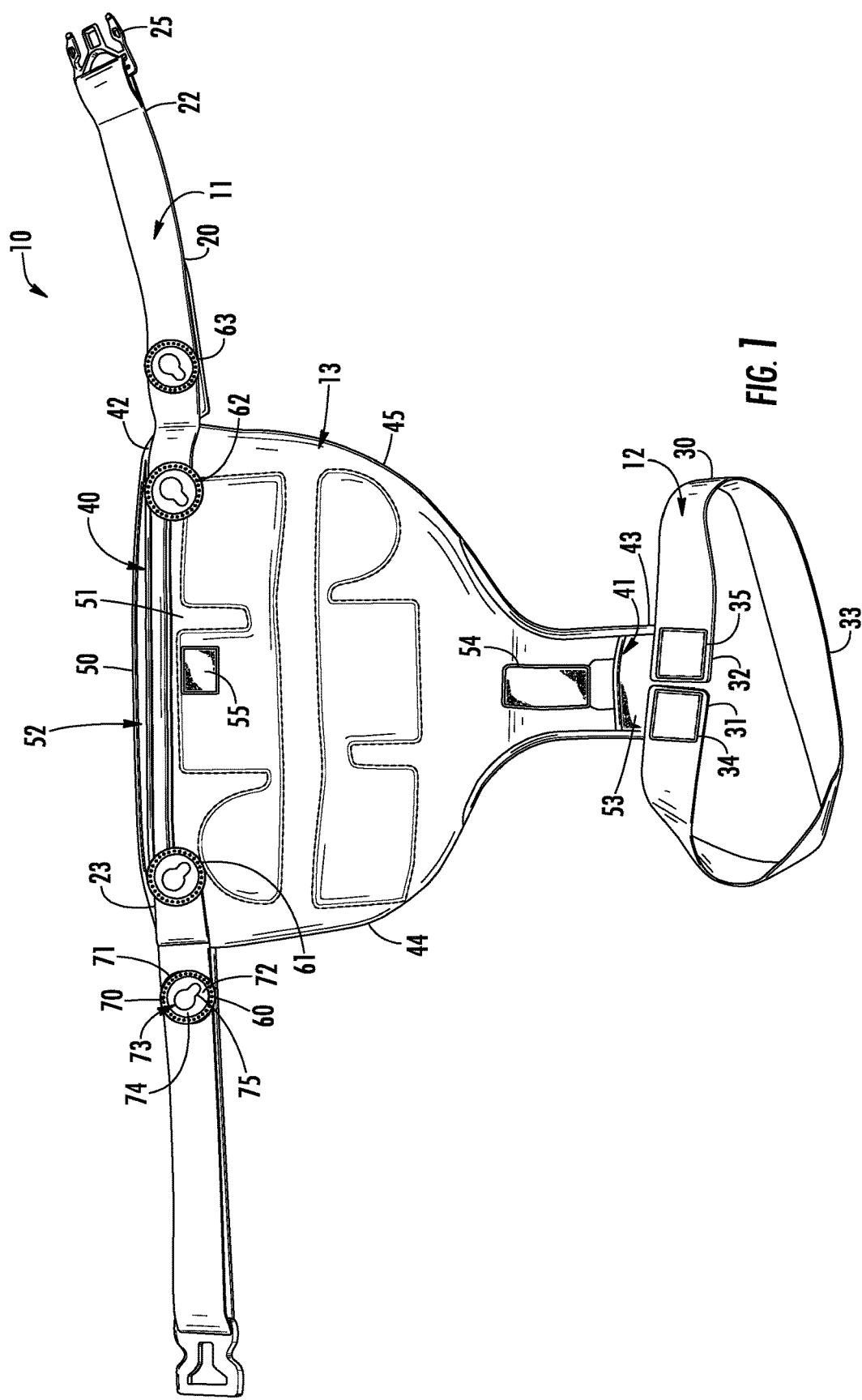
FIG. 1 is an elevation view of an improved pain management and post-operative hip orthosis, illustrating a waist strap, a lower strap, and a pocket therebetween.

Reference now is made to the drawings, in which the same reference characters are used throughout the different figures to designate the same elements. FIG. 1 illustrates an improved pain management and post-operative hip orthosis 10 (hereinafter, "orthosis 10"). The orthosis 10 is shown throughout the drawings in various arrangements, with various accessories and appliances attached to it in differing combinations. Though shown in differing combinations with various accessories and appliances, reference is made to the orthosis 10 consistently to identify the entire structure.

As shown in FIG. 1, the orthosis 10 includes a waist strap 11, a lower strap 12, and a pocket 13 extending between the waist strap 11 and the lower strap 12. The waist strap 11, lower strap 12, and pocket 13 define a platform upon which all the accessories and appliances are placed and attached, as is described herein.

In the embodiment shown in these drawings, the waist strap 11 has a body 20 constructed from an elastic webbing. The body 20 of the waist strap 11 has opposed first and second ends 21 and 22 and a lateral portion 23 therebetween. The elastic webbing is doubled on itself to provide the waist strap 11 with two plies or layers. Proximate the first end 21, the two plies of the elastic webbing are loose and free of each other, while proximate the second end 22, the two plies of the elastic webbing are secured to each other, such as by stitching, stapling, sonic welding, or other similar fastening means. The elastic webbing is dynamic, elastic, resilient, and has shape memory along its entire length between the first and second ends 21 and 22. The first end 21 of the waist strap 11 is fit with a female buckle element 24 and the second end 22 of the waist strap 11 is fit with a complemental male buckle element 25. The first and second ends 21 and 22 may be coupled to each other with these buckle elements 24 and 25, but in other embodiments, could be coupled with hook-and-loop engagement elements, snap closures, buttons, or other similar coupling means. While the female buckle element 24 can be slid on the two loose plies of the waist strap 11 between the first end 21 and the lateral portion 23 to adjust the length and fit of the waist strap 11, the male buckle element 25 is loosely secured at the second end 22 by the stitching, which is located just behind the second end 22.

The lower strap 12 also has a body 30 constructed from an elastic webbing, and the body 30 has opposed first and second ends 31 and 32 and a lateral portion 33 therebetween. The elastic webbing is preferably a single layer, though in some embodiments, it may be doubled back on itself like that of the waist strap 11. The elastic webbing is dynamic, elastic, resilient, and has shape memory along its entire length between the first and second ends 31 and 32. The first end 31 of the lower strap 12 carries a hook-and-loop engagement element 34, and the second end 32 of the lower strap 12 carries a complemental hook-and-loop engagement element 35. The first and second ends 31 and 32 are coupled to each other with these hook-and-loop elements 34 and 35, but in other embodiments, could be coupled with complemental buckle elements, snap closures, buttons, or other similar coupling means.

The pocket 13 extends between the waist and lower straps 11 and 12. The pocket 13 is a flexible pocket, tapered from a wide upper opening 40 at a top 42 of the pocket 13 to a narrow lower opening 41 proximate to the bottom 43 of the pocket 13, and is capable of bending, rolling, and otherwise flexing between and across the top 42 and bottom 43. The pocket 13 has opposed first and second sides 44 and 45 extending entirely between the top 42 and bottom 43.

The pocket 13 is constructed from two flexible panels: a first or inner panel 50 and a second or outer panel 51. The inner and outer panels 50 and 51 are fastened to each other, preferably by stitching extending along the first and second sides 44 and 45. The inner and outer panels 50 and 51 are not continuously fastened to each other at the top 42 or the bottom 43, thereby defining the upper and lower openings 40 and 41, respectively. The upper opening 40 is opened entirely between the first and second sides 44 and 45 at the top 42, and the lower opening 41 is opened entirely between the first and second sides 44 and 45 at the bottom 43. Nevertheless, because of the tapered shape of the pocket 13, the upper opening 40 is much larger than the lower opening 41. Though it is open, the upper opening 40 can nevertheless be closed by complemental hook-and-loop engagement member on its inner surfaces, or by a clasp or button closure, slideable fastenere, or other similar fastening mechanism.

The pocket 13 is shaped like a truncated hourglass, severed at its midsection. As such, the pocket 13 is quite wide at the top 42. The first and second sides 44 and 45 extend downward nearly perpendicular from the top 42, nearly parallel to each other. The first and second sides 44 and 45 then turn inward, converging toward each other at a location generally intermediate the top 42 and bottom 43. Then, just above the bottom 43, the first and second sides 44 and 45 turn downward again and nearly parallel to each other again, where they terminate just below the lower opening 41. The lower opening 41 has a width between the first and second sides 44 and 45 which is approximately one-fifth the width of the upper opening 40.

The lower opening 41 is actually just above the bottom 43 of the pocket 13. The lower opening 41 is a slot formed between the inner and outer panels 50 and 51, but the outer panel 51 terminates above the lower edge of the inner panel 50. In other words, the inner panel 50 extends slightly below or lower than the outer panel 51.

Both the upper and lower openings 40 and 41 lead to an interior 52, defined between the inner and outer panels 50 and 51. The interior 52 has a shape or profile corresponding to that of the pocket 13, and the interior 52 is slim between the inner and outer panels 50 and 51. The interior 52 is thus configured to snugly receive a cooling pack, as will be described.

Still referring to FIG. 1, there are various attachment points on the pocket 13. At the bottom 43 of the pocket 13, a hook-and-loop engagement element 53 is positioned on the inner panel 50, facing outward. The engagement element 53 is positioned below the lower edge of the outer panel 51 and above the lower edge of the inner panel 50, so that its full extent is exposed and available for placement of a complemental hook-and-loop engagement element. Indeed, the hook-and-loop engagement elements 34 and 35 of the first and second ends 31 and 32 of the lower strap 12 are secured on this engagement element 53 at the bottom 43 of the pocket 13, so that the lower strap 12 is secured at this location as an anchor point.

Two more engagement elements 54 and 55 are carried on the exterior of the outer panel 51. Engagement element 54 is a lower engagement element 54, located just above the engagement element 53. This lower engagement element 54 is elongate, longer in a vertical direction than in a horizontal direction. The engagement element 55—an upper engagement element 55—is registered along a vertical line with the lower engagement element 54. The upper engagement element 55 is roughly square-shaped and is located just below the upper opening 40. The lower and upper engagement elements 54 and 55 are located generally intermediately between the first and second sides 44 and 45. The lower and upper engagement elements 54 and 55 are available to secure an articulating brace thereon, as is described below.

Proximate the top 42 of the pocket 13, four round elements are carried on the orthosis 10 for securing various attachments and accessories. These are key-hole receivers 60-63, and each is identical. As such, only the key-hole receiver 60 will be described, with the understanding that the description applies equally to each receiver 60-63. The key-hole receiver 60 includes a round, flat base 70 with a circular perimeter 71. The base 70 includes a raised dome 72 formed with a slot 73. The slot 73 includes an enlarged entrance 74 and a narrowed catch 75. Each attachment and accessory which is secured to the orthosis 10 includes a post which engages with the key-hole receivers 60-63. The key-hole receivers 60-63 are angled toward the middle and bottom 43 of the pocket 13: since the key-hole receivers 60 and 61 flank the pocket 13, or are "in front" of the pocket 13 and the key-hole receivers 62 and 63 are "behind" the pocket 13 (when worn on a patient's left hip), the key-hole receivers 60 and 61 are angled differently than the key-hole receivers 62 and 63. Stitching extends through the holes in the perimeter 71 to attached the key-hole receives 60-63 to the orthosis 10; the receivers 60 and 63 are sewn onto the waist strap 11, and the receivers 61 and 62 are sewn onto the exterior of the outer panel 51.

Figure 2:
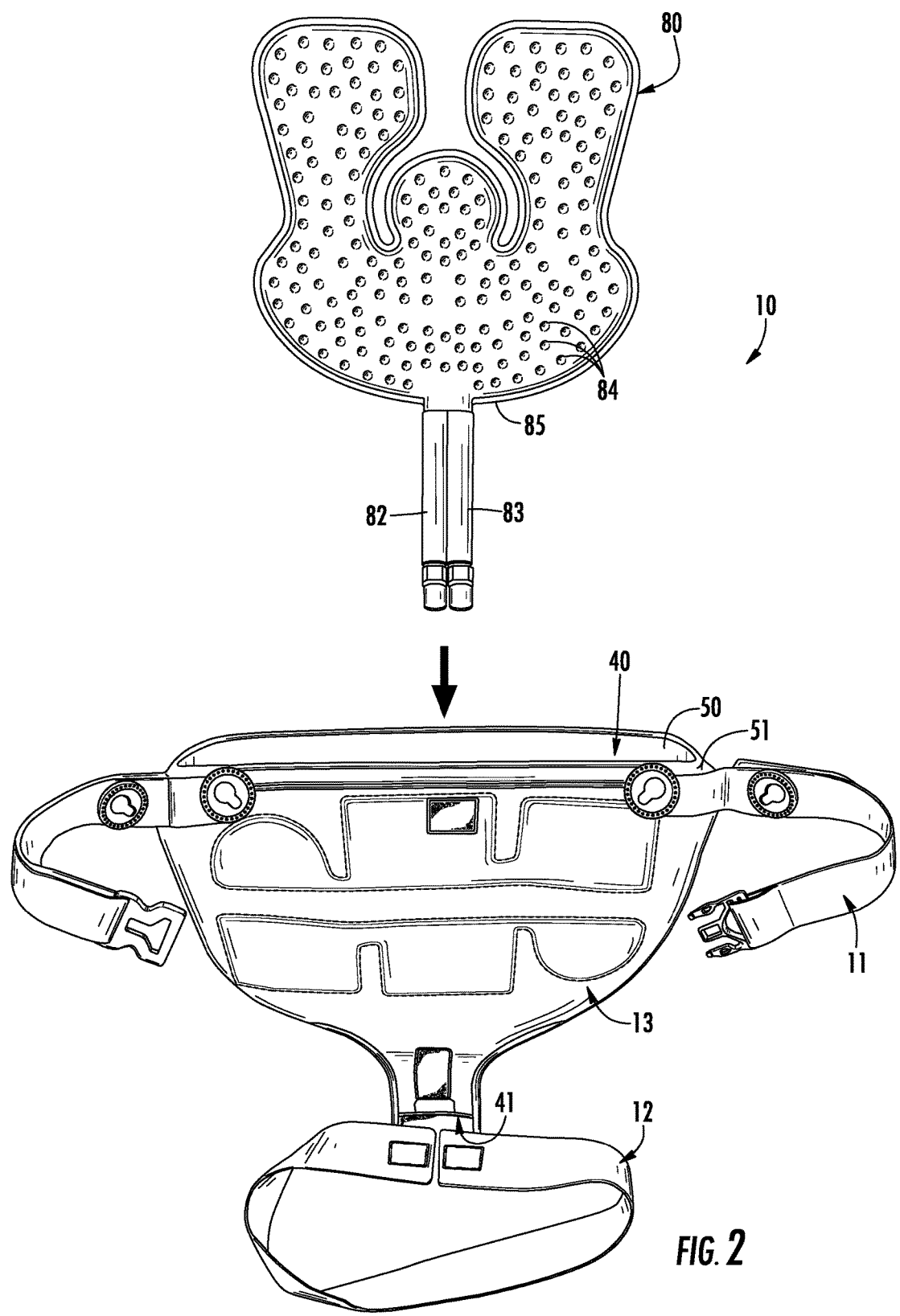
FIG. 2 is an elevation view of the orthosis of FIG. 1, with a cooling pack above an upper opening of the pocket, ready to be applied to the pocket.

The description now turns to FIG. 2, which is an elevation view of the orthosis 10 showing a cooling pack 80 above the upper opening 40 of the pocket 13 and ready to be applied to the pocket 13 to define part of the orthosis 10. The upper opening 40 is opened slightly more than in FIG. 1, showing the separation between the inner panel 50 and the outer panel 51.

The cooling pack 80 includes a sealed bladder or reservoir 81 and inlet and outlet tubes 82 and 83 for circulating fluid into and out of the reservoir 81. In some embodiments, the reservoir 81 is formed with internal routing or channels, to route the fluid through the reservoir 81 in particular directions. In this embodiment, however, the reservoir 81 is simply formed with a plurality of spot welds 84 holding front and back panels of the reservoir 81 together across its area. The reservoir 81 has a roughly horseshoe-shaped design, but any suitable design is appropriate. The inlet and outlet tubes 82 and 83 extend out from the bottom 85 of the cooling pack 80 so that they may be threaded through the lower opening 41 of the pocket 13 and thus coupled through another tubing set to a cooling machine.

Figure 3:
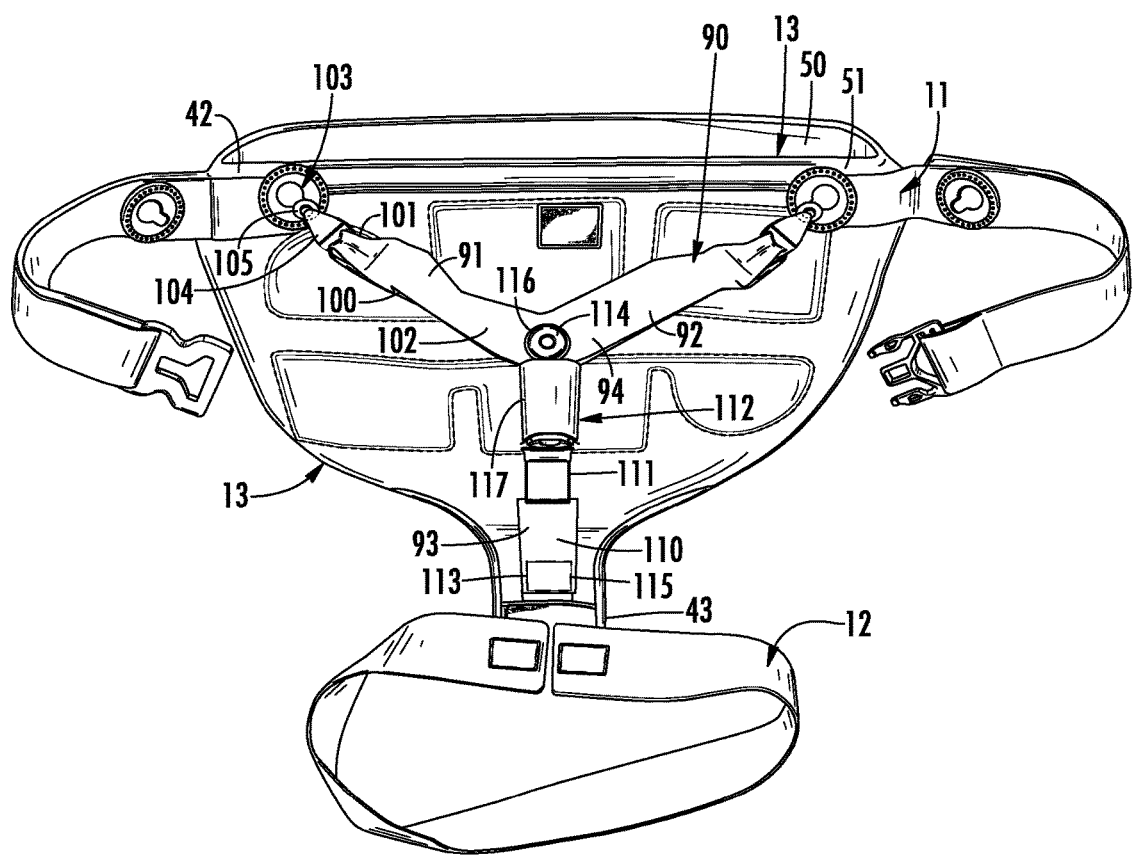

FIG. 3 is an elevation view of the orthosis 10 with an abduction harness 90 applied thereon and forming part of the orthosis 10. The abduction harness 90 is suitable to abduct a leg, or pull the leg outward away from the centerline of the body. The abduction harness 90 includes two opposed upper straps 91 and 92 and an opposed lower strap 93 coupled to each other at a central union 94 so that the lower strap 93 can outwardly pull the bottom 43 of the pocket 13. The upper straps 91 and 92 are secured to the top 42 of the pocket 13, and the lower strap 93 is secured to the bottom 43 of the pocket 13.

The upper straps 91 and 92 are identical to each other in structure and only the upper strap 91 will be described with the understanding that the description applies equally to the strap 92. The upper strap 91 has a body 100 constructed from an inelastic webbing with a free or first end 101 and an opposed second end 102 formed integrally and monolithically to the central union 94. The first end 101 is fit with a post engagement element 103 complemental to the key-hole receivers 60-63. The post engagement element 103 includes a base 104 and a post 105 projecting from the base 104. The post 105 is circular, just slightly narrower than the enlarged entrance 74 of the key-hole receiver 60, and just slightly larger than the narrowed catch 75 to which it engages. The post 105 projects slightly forwardly and downwardly from the base 104 so as to be spaced apart from the base 104, in such a way that the post 105 can slide into the enlarged entrance 74. Then, pulling the post 105 downward causes the post 105 to slide into the narrowed catch 75 and become lodged therein, where it cannot be inadvertently removed from the slot 73. Further, because the forces exerted along the upper straps 91 and 92 are from below, the posts 105 are constantly pulled downward, into the catch 75, and as such are unlikely to become disengaged from the key-hole receivers 60-63. Still further, the post and key-hole engagement allows the upper straps 91 and 92 to pivot or swing slightly from the catch 75, which provides the engagement with flexibility as a patient walks with the abduction harness 90 on the orthosis 10.

The other upper strap 92 is identical to the upper strap 91, but extends oppositely away from the central union 94. The upper straps 91 and 92 extend away from the central union 94 at approximately 120 degrees with respect to each other. The lower strap 93 extends downwardly from the central union 94 at approximately 120 degrees with respect to each of the upper straps 91 and 92. The lower strap 93 has a body constructed from an inelastic webbing 110, an elastic webbing 111, and an expansion assembly 112 joined together to form a single length. The body of the lower strap 93 extends from a free or first end 113 to an opposed second end 114 secured on the central union 94. The inelastic webbing 110 is proximate the first end 113, the expansion assembly 112 is proximate the second end 114, and the elastic webbing 111 is between the inelastic webbing 110 and the expansion assembly 112.

Still referring to FIG. 3, the inelastic webbing 110 is a short run of webbing having resiliency and durability. It carries a patch of hook-and-loop engagement element 115 on its underside, adapted to engage with the outwardly-disposed long upper engagement element 54 (obscured by the engagement element 115) on the pocket 13. This engagement secures the first end 113 of the abduction harness 90 on the pocket 13. The top of the inelastic webbing 110 is fixed to the elastic webbing 111, which is dynamic, elastic, resilient, and has shape memory along its entire length. The inelastic webbing 110 is rugged and durable, but stretches slightly. It is, in turn, fixed to the expansion assembly 112, which includes a short run of webbing, a cord laced through pulley or sleeves, and a ratcheting rotational tightening mechanism 116 (such as the kind sold under the BOA® trademark) through which the cord is secured. The short run of webbing and cord are covered and protected by a sleeve 117, and the ratcheting rotational tightening mechanism 116 is exposed on the other side of the sleeve 117, where it is fixed to the central union 94, thereby fixing the lower strap 93 to the central union 94. The length of the lower strap 93 can then be adjusted by rotating the ratcheting rotational tightening mechanism 116 to shorten the length, or by releasing the ratcheting rotational tightening mechanism 116 to lengthen the lower strap 93. Adjusting the length of the lower strap 93 adjusts the degree to which the abduction harness 90 abducts the leg.

Figure 4:
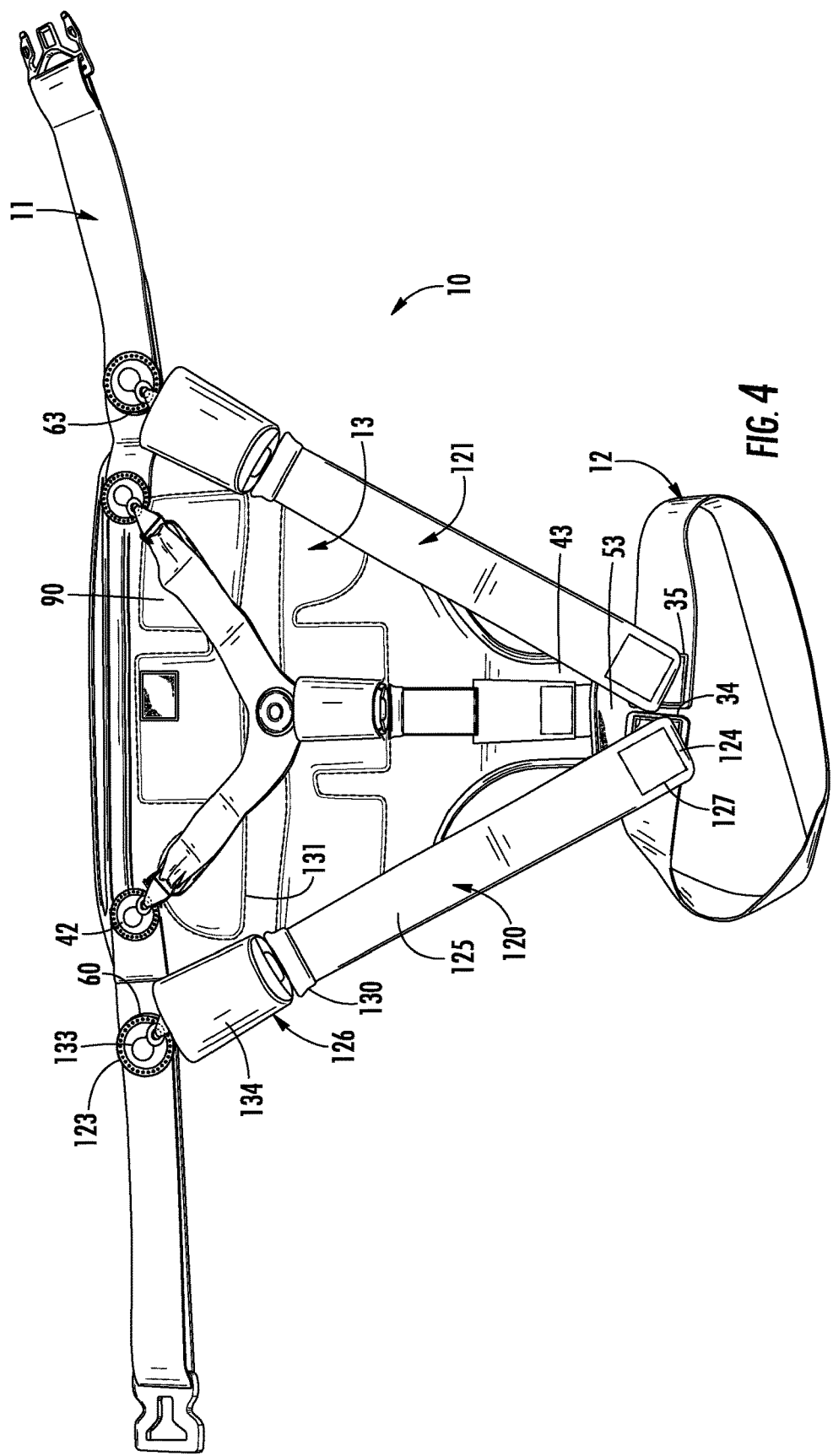

FIG. 4 is an elevation view of the orthosis 10 with two rotation straps 120 and 121 applied thereon and forming part of the orthosis 10. FIG. 4 also illustrates the abduction harness 90 applied to the orthosis 10. Each of the rotation straps 120 and 121 is suitable to rotate or turn a leg, such by internally or externally rotating the leg. In practice, both rotation straps 120 and 121 would likely not be used at the same time; rather, one rotation strap would be used to rotate the leg internally or externally, or to prevent flexion or extension of the leg, as will be described. Indeed, in the embodiment shown in FIG. 4, the rotation straps 120 and 121 are counteracting each other. Nevertheless, this is shown so that the drawing illustrates the alternate arrangements of the rotation straps 120 and 121.

The rotation straps 120 and 121 are identical in every way and are identified by different reference characters only because of their different locations and arrangements. As such, only the rotation strap 120 is described, and it should be understood that the description applies equally to the rotation strap 121. The rotation strap 120 has a body 122 with free, opposed, first and second ends 123 and 124. The first end 123 is an upper end of the rotation strap 120 and is secured to the waist strap 11 proximate to the top 42 of the pocket 13 with a key-hole engagement, and the second end 124 is a lower end of the rotation strap 120 and is secured to the bottom 43 of the pocket 13 with a hook-and-loop engagement. The body 122 is constructed from an inelastic webbing 125 secured to an expansion assembly 126. The inelastic webbing 125 constitutes the majority of the length of the rotation strap 120. The second end 124 carries a patch of hook-and-loop engagement element 127 on its underside, which is engaged with the outwardly-disposed complemental hook-and-loop engagement element 34 on the lower strap 12. In some arrangements, the engagement element 127 of the rotation strap 120 may be applied to the hook-and-loop engagement element 53 carried directly on the bottom 43 of the pocket 13. Opposite this, the inelastic webbing 125 is fixed to the expansion assembly 126.

Like the expansion assembly 112, the expansion assembly 126 includes a short run of webbing 120, a cord 131 laced through pulleys 132 or sleeves, and a ratcheting rotational tightening mechanism 133 (such as the kind sold under the BOA® trademark) through which the cord 131 is secured. The short runs of webbing 130 and cord 131 are covered and protected by a sleeve 134, and the ratcheting rotational tightening mechanism 133 is exposed on the other side of the sleeve 134 where it is engaged to the key-hole receiver 60. The ratcheting rotational tightening mechanism 133 has a post on its underside which engages with and lodges in the narrowed catch 75 of the receiver 60, similar to the post the upper straps 91 and 92. This engagement fixes the rotation strap 120 to the waist strap 11. The length of the rotation strap 120 can then be adjusted by rotating the ratcheting rotational tightening mechanism 133 to shorten the length, or by releasing the ratcheting rotational tightening mechanism 133 to lengthen the rotation strap 120. Adjusting the length of the rotation strap 120 adjusts the degree to which the rotation strap 120 rotates the leg or limits flexion and extension movement. The rotation strap 120, when arranged and secured between the key-hole receiver 60 and the hook-and-loop engagement element 34, operates two affect both the rotation of the leg and the flexion or extension of the leg. First, the rotation strap 120 internally rotates the leg, or turns the leg so that the knee rotates inwardly toward the centerline of the body. Tightening the ratcheting rotational tightening mechanism 133 increases the amount of this rotation. Second, the rotation strap 120 limits or even prevents extension of leg, depending on the tightness of the rotation strap 120; extension of the leg is movement of the leg behind the body. When the orthosis 10 is worn on the left hip, the rotation strap 120 extends from the lateral portion of the leg toward the front of the body, and so it rotates the leg inwardly and prevents rearward extension of the leg. When worn on the right hip, an opposite effect is achieved. When a rotation strap is placed oppositely, as the rotation strap 121 is, between the key-hole receiver 63 and the hook-and-loop engagement element 35, the rotation strap 121 operates to externally rotate the leg, or rotate the leg so that the knee moves away from the centerline of the body. Further, it limits or prevents flexion of the leg; flexion of the leg is movement of the leg in front of the body. When the orthosis is worn on the left hip and the rotation strap 121 is used alone, the rotation strap 121 not only externally rotates the leg but also limits the extent to which the patient can move the flexion, i.e., in front of the body. When worn on the right hip, an opposite effect is achieved.

Figure 10:
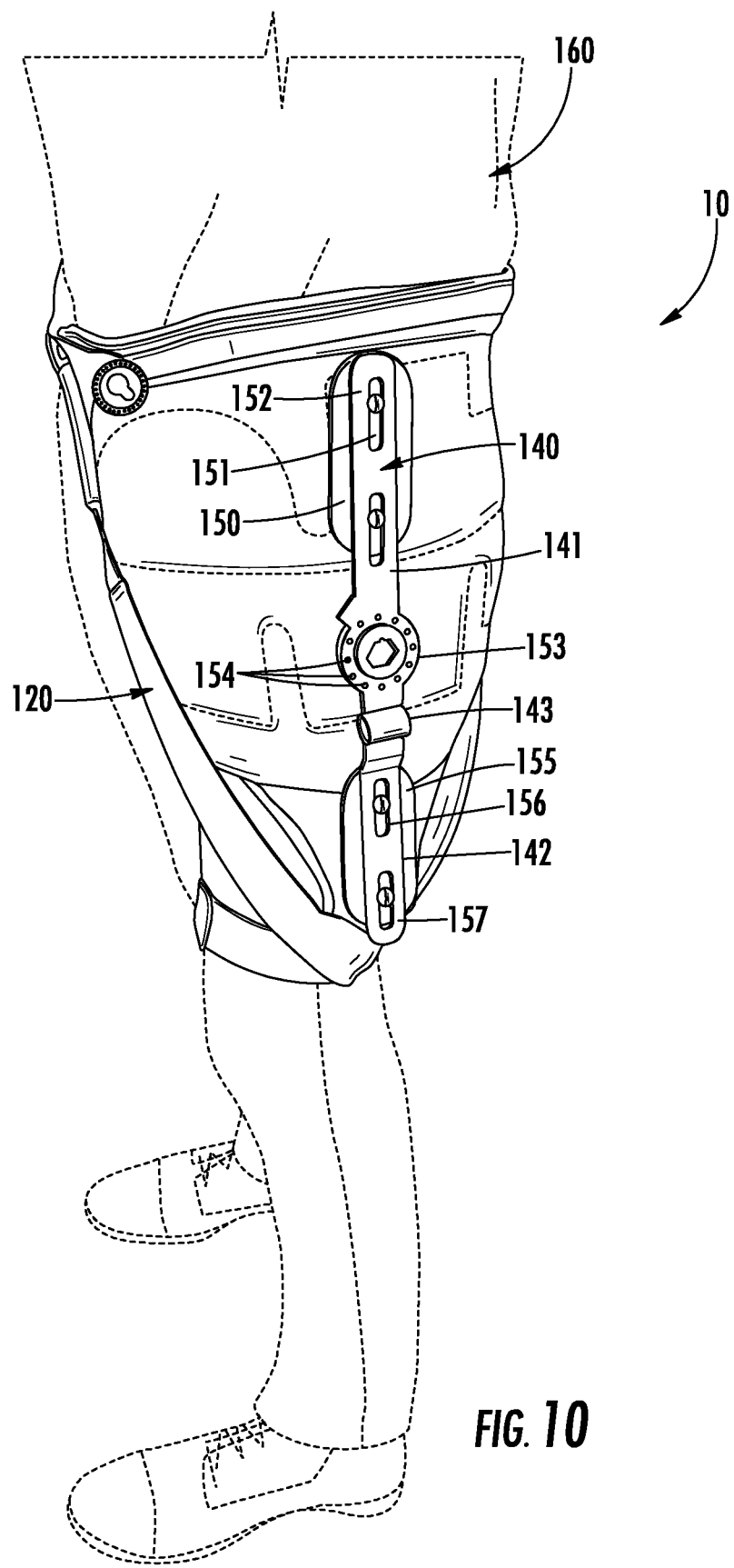
FIG. 10 is a side perspective showing the orthosis of FIG. 1 worn on a patient, with a rotation strap and the articulating brace.

Turning now to FIG. 5 and FIG. 10, the orthosis 10 is shown with an articulating brace 140 applied thereto. In FIG. 5, the orthosis 10 also carries the abduction harness 90 and the two rotation straps 120 and 121; in FIG. 10, the abduction harness 90 is removed. The description below refers primarily to FIG. 10. The articulating brace 140 is a semi-rigid brace for limiting flexion movement of the leg. The brace 140 includes a rigid upper member 141 and an opposed rigid lower member 142 coupled to each other at a hinge 143.

The upper member 141 includes a pad 150 and a pair of longitudinal slots 151 formed through a rigid body 152 of the upper member 141. Fasteners, such as bolts, couple the pad 150 to the body 152, and the fasteners can be slid within the slots 151 and then tightened to adjust the fit of the upper member 141. The upper member 141 further includes a pivot 153. The pivot 153 allows flexion of the leg at the hip to a preset degree. Stops 154 arranged about the perimeter of the pivot 153 can be selected by an attending physician to limit the extent of the flexion movement. An arm extending out of the bottom of the pivot 153 cooperates with the lower member 142 to form the knuckles of the hinge 143. The hinge 143 can also be set by a physician to aid in abduction or adduction of the leg.

The lower member 142 includes a pad 155 and a pair of longitudinal slots 156 formed through a rigid body 157 of the lower member 142. Fasteners, such as bolts, couple the pad 155 to the body 157, and the fasteners can be slid within the slots 156 and then tightened to adjust the fit of the lower member 142.

Figure 6A:
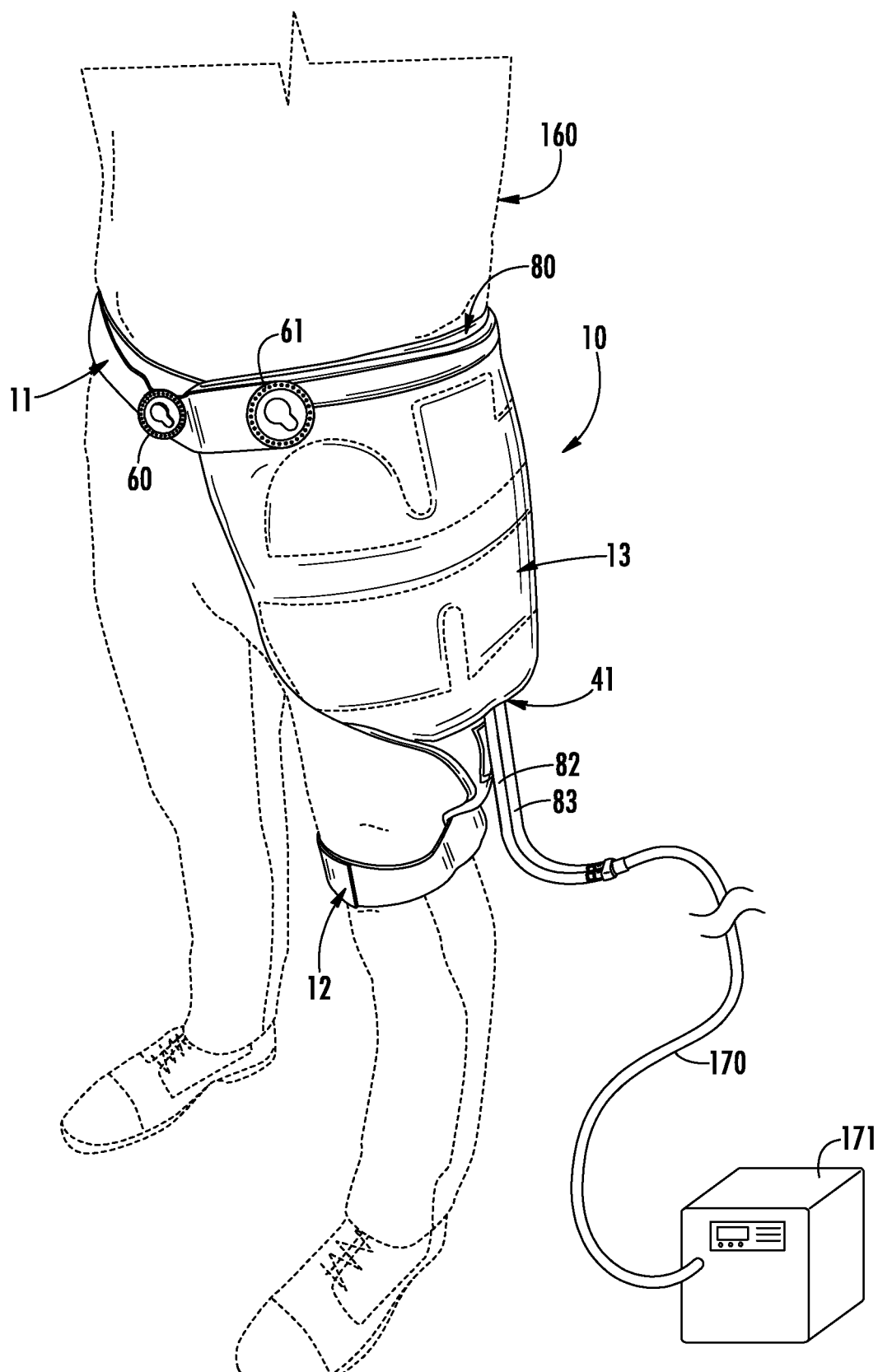
FIGS. 6A and 6B are front and back perspectives, respectively, showing the orthosis of FIG. 1 worn on a patient, with the cooling pack applied to the pocket of the orthosis.
Figure 6B:
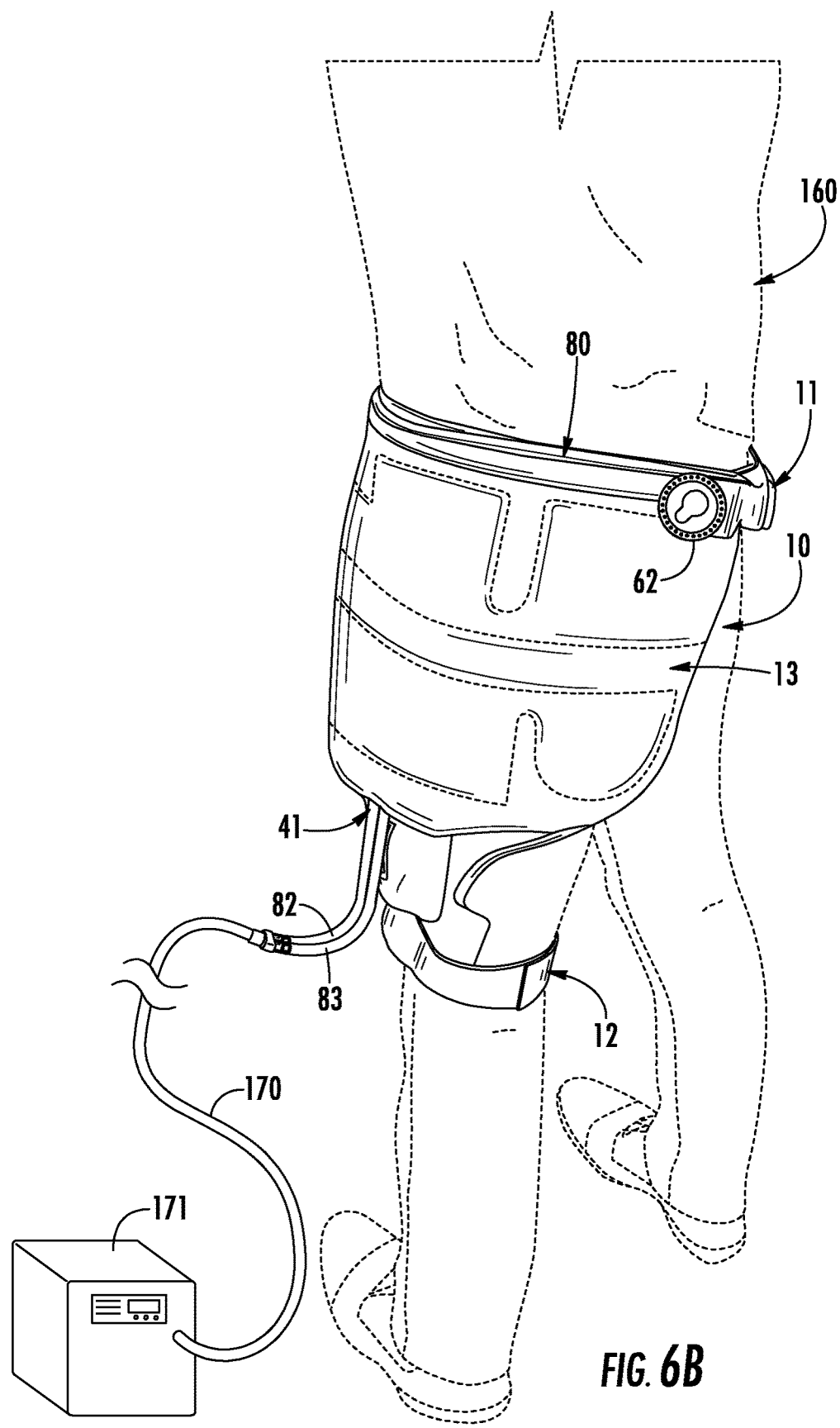

FIGS. 6A and 6B show the orthosis 10 worn on the hip of a patient 160. The cooling pack 80 is applied to the interior 52 of the pocket 13, with the inlet and outlet tubes 82 and 83 extending out of the lower opening 41 of the pocket 13, connected to supply lines 170 which in turn extend to a powered cooler 171. The waist strap 11 is secured about the waist of the patient 160, and the lower strap 12 is secured about the leg of the patient 160, just above the knee. Both the waist strap 11 and the lower strap 12 are adjusted so that they snugly fit around the patient 160. This allows the patient 160 to stand with the orthosis 10 on and without it falling off, and also to lie supine without the orthosis 10 moving off the hip. When the cooler 171 is activated, cool fluid is pumped up from the cooler 171 through one of the supply lines 170 and into the inlet tube 82, where it enters the reservoir 81 of the cooling pack 80. The cool fluid circulates throughout the reservoir 81 and then returns to the cooler 171 via the outlet tube 83. This provides cooling therapy to the hip.

Figure 7A:
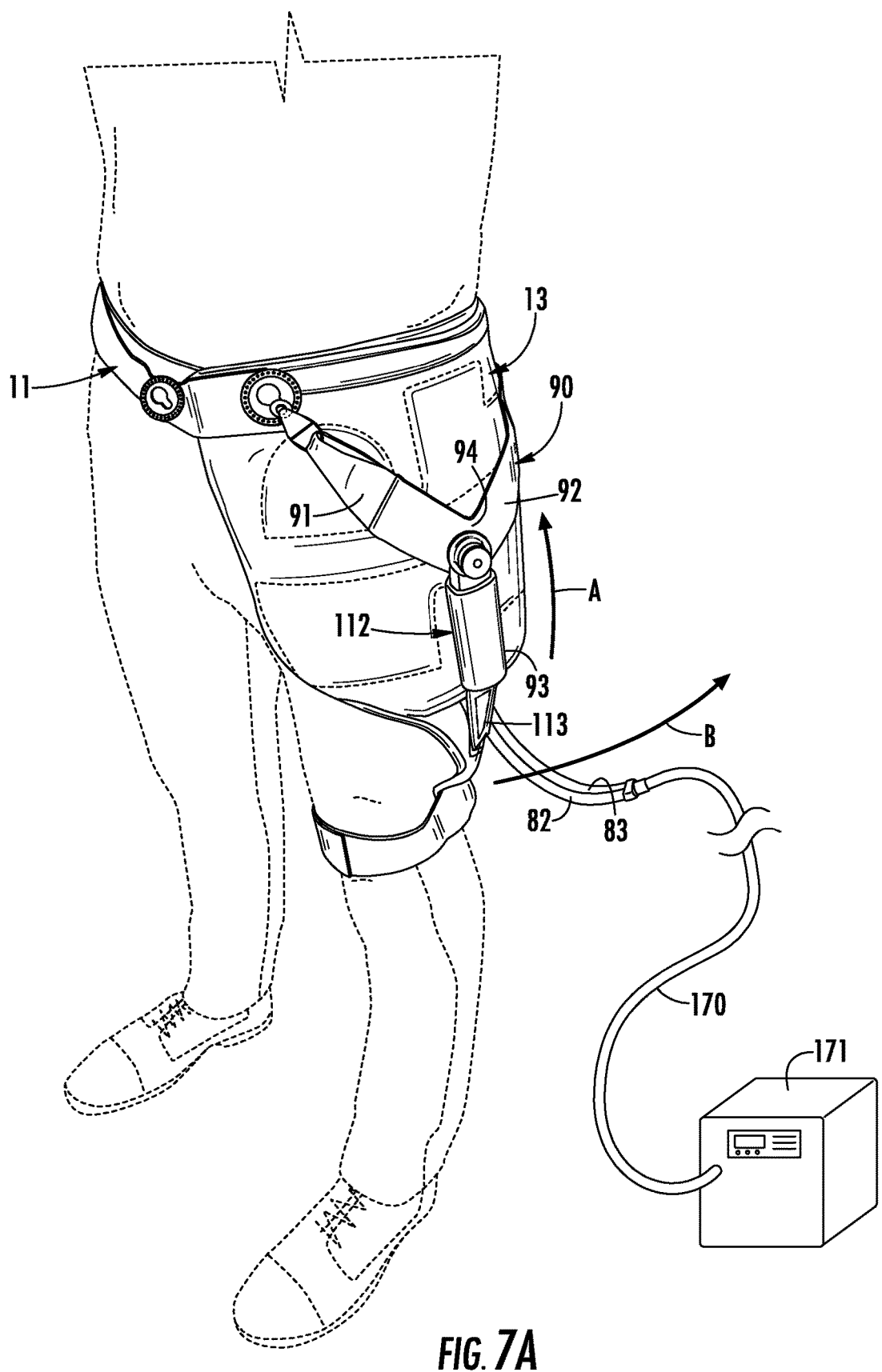
FIGS. 7A and 7B are front and back perspectives, respectively, showing the orthosis of FIG. 1 worn on a patient, with the cooling pack and the abduction harness.
Figure 7B:
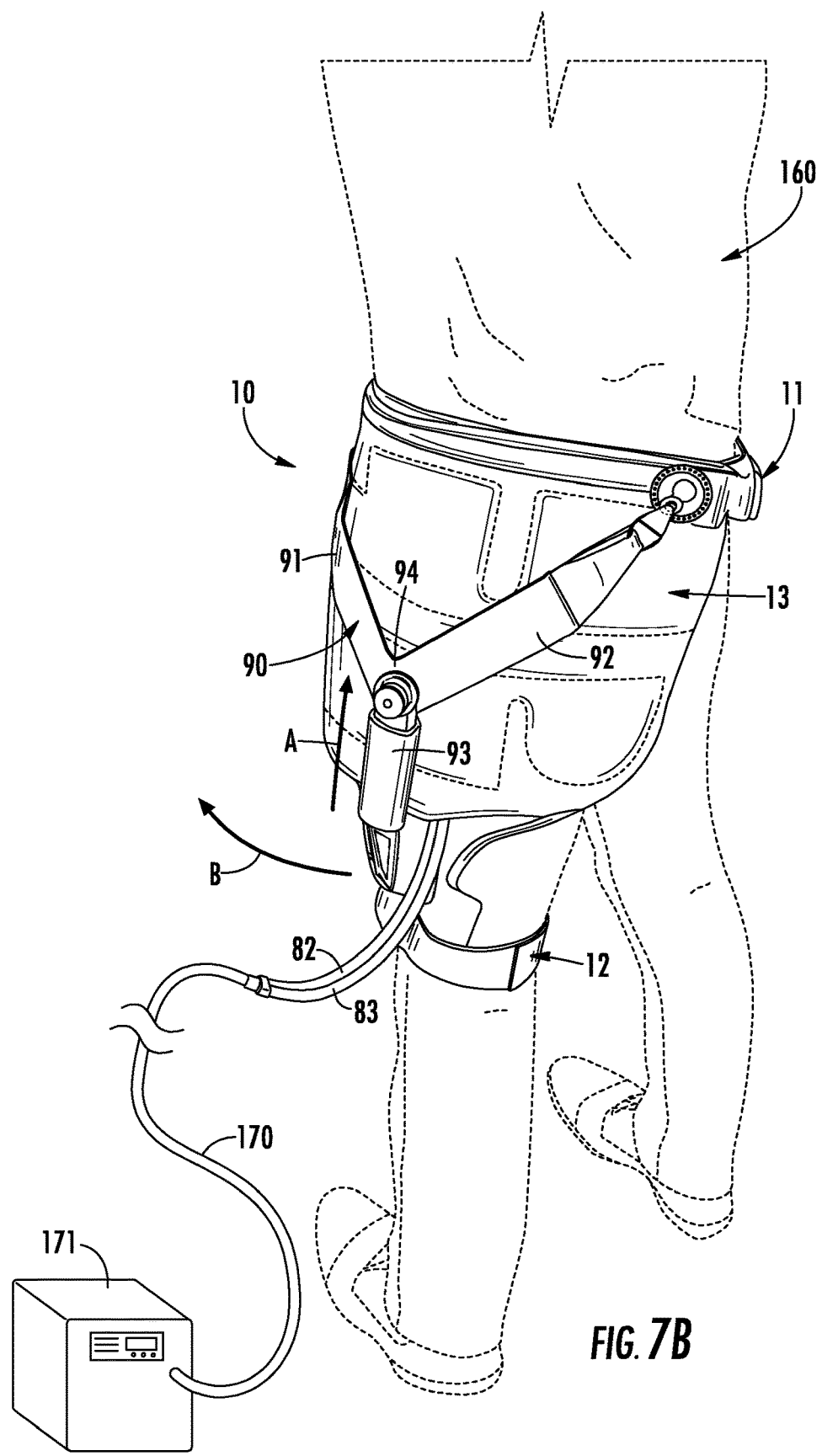

Turning now to FIGS. 7A and 7B, the patient 160 is shown from front and rear perspectives, respectively, wearing the orthosis 10. Here, the orthosis 10 carries the cooling pack 80 and the abduction harness 90. The expansion assembly 112 of the lower strap 93 of the abduction harness 90 has been tightened along line A, thereby pulling the lower or first end 113 of the lower strap 93 upward along line A. This abducts the leg outwardly, along arcuate line B. It is noted that line B is exaggerated and meant only to show the direction of abduction and not the amplitude or amount of abduction. When the patient 160 is standing, supine, or in some other position, the abduction harness 90 pulls the leg outwardly along line B to promote recovery.

Figure 8:
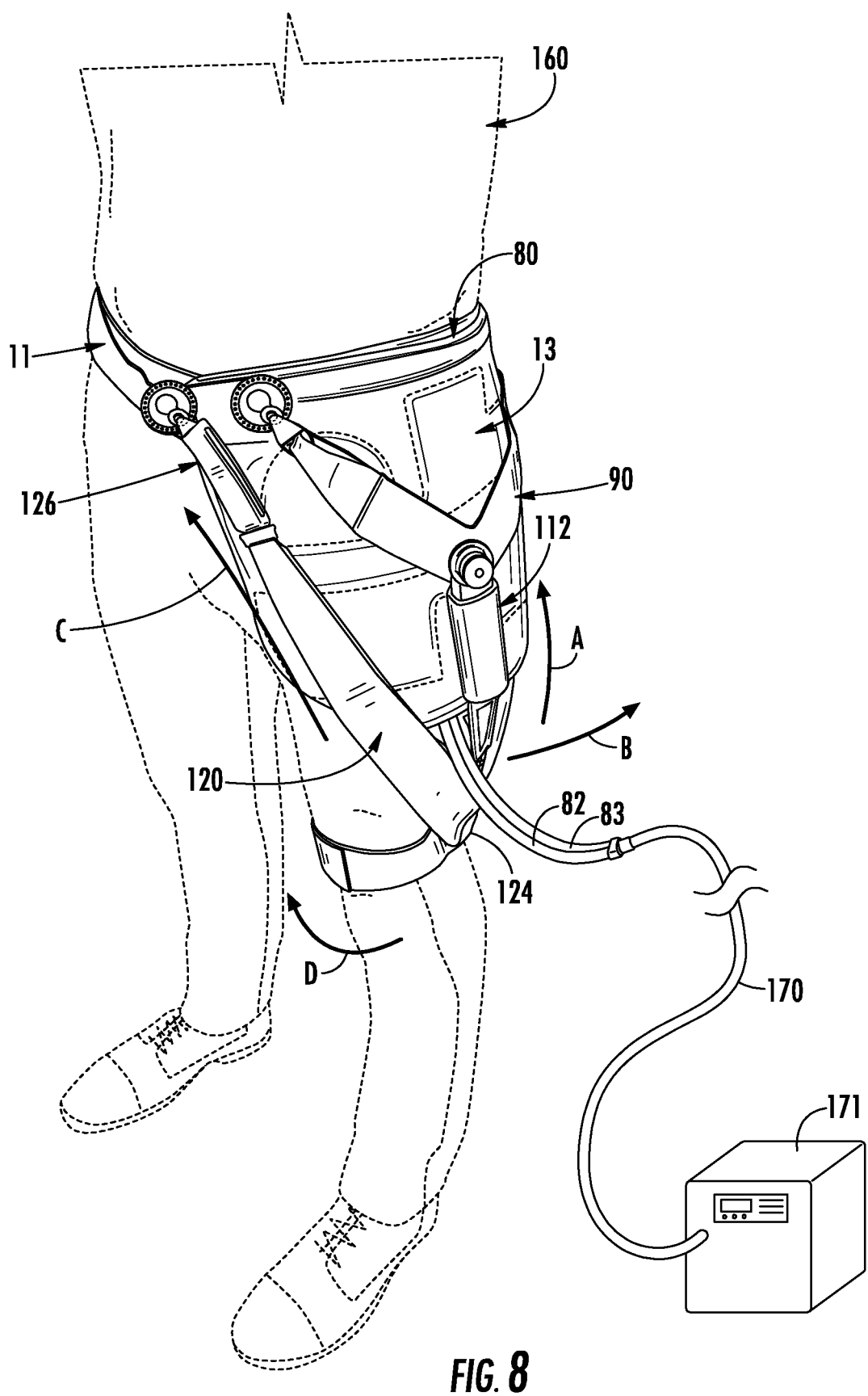
FIG. 8 is a front perspective showing the orthosis of FIG. 1 worn on a patient, with the cooling pack, abduction harness, and a rotation strap.

FIG. 8 is a front perspective view of the orthosis 10 worn by the patient 160, with the cooling pack 80, the abduction harness 90, and the rotation strap 120 all applied. The expansion assembly 112 of the abduction harness 90 maintains its state of tightness, and the abduction harness 90 continues to bias the leg outwardly along line B. Further, the cooling pack 80 provides cool therapy to the hip. Moreover, the rotation strap 120 is adjusted to internally rotate the leg and limit extension of the leg. The expansion assembly 126 of the rotation strap 120 is tightened, pulling the second end 124 of the rotation strap 120 upward toward the waist strap 11. Because the rotation strap 120 crosses diagonally across the pocket 13 from proximate to the bottom 43 near the lateral side of the knee to the waist strap 11 proximate the belly button of the patient 160, the rotation strap 120 imparts a rotational bias on the leg, causing it to rotate internally along the line D. Further, the rotation strap 120 prevents the leg from moving rearwardly too far, and so the rotation strap 120 limits extension of the leg. Referring briefly to FIG. 4, if the rotation strap 121 were used instead of the rotation strap 120, rotation of the leg would be in a direction opposite to the line D and flexion of the leg would be limited.

Figure 9:
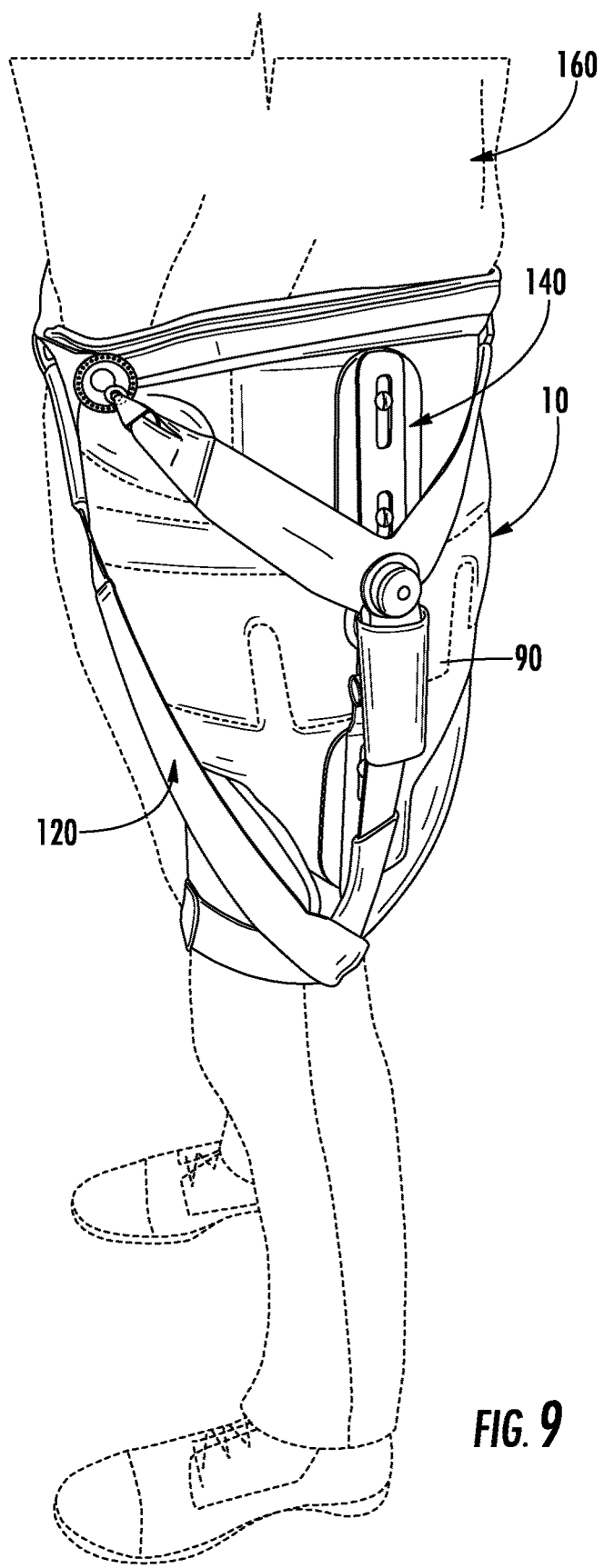
FIG. 9 is a side perspective showing the orthosis of FIG. 1 worn on a patient, with the abduction harness, a rotation strap, and the articulating brace.

FIG. 9 is a side perspective view of the orthosis 10. Here, the cooling pack 80 is removed, but the abduction harness 90, the rotation strap 120, and the articulating brace 140 are all in place. When used in this arrangement, the patient 160 is free to walk around without limitation while wearing the orthosis 10. The abduction harness 90 maintains an abducting bias on the leg, the rotation strap 120 ensures the leg will not twist outwardly and will not extend fully rearwardly, and the articulating brace 140 prevents the patient 160 from over-extending his leg about the hip joint. Ambulatory therapy such as this, in a controlled manner, is beneficial to recovery after lower leg procedures.

Finally, in FIG. 10, as discussed briefly above, the orthosis 10 is shown in a side perspective with only the rotation strap 120 and articulating brace 140 applied thereto. This arrangement may be prescribed by a physician to allow the patient 160 abduction and adduction flexibility in the frontal plane, but to prevent external rotation of the leg and to limit extension and flexion of the hip joint. As FIGS. 6A-10 illustrate, a variety of arrangements of the orthosis 10 and its accessories and attachments are possible, each providing a different combination of flexibility, support, and therapeutic benefits.

A preferred embodiment is fully and clearly described above so as to enable one having skill in the art to under-stand, make, and use the same. Those skilled in the art will recognize that modifications may be made to the description above without departing from the spirit of the invention, and that some embodiments include only those elements and features described, or a subset thereof. To the extent that modifications do not depart from the spirit of the invention, they are intended to be included within the scope thereof.

The invention claimed is:

1. An orthosis comprising:
   a waist strap having opposed first and second ends and a lateral portion therebetween, the first and second ends having coupling means for coupling the first and second ends;
   a lower strap having opposed first and second ends and a lateral portion therebetween, the first and second ends of the lower strap having coupling means for coupling the first and second ends of the lower strap;
   a pocket extending between the waist strap and the lower strap, the pocket comprising an inner panel and an outer panel fastened to each other to define an upper opening at a top of the pocket and a lower opening at a bottom of the pocket, the upper opening larger than the lower opening; and
   an abduction harness, for laterally abducting a leg, comprising two upper straps and a lower strap coupled to each other at a central union, wherein the upper straps are secured to the top of the pocket, and the lower strap is secured to the bottom of the pocket;
   wherein the top of the pocket is secured to the lateral portion of the waist strap, and the first and second ends of the lower strap are secured on the bottom of the pocket.

2. The orthosis of claim 1, further comprising a rotation strap extending from the bottom of the pocket to a location on the waist strap proximate to the top of the pocket.

3. The orthosis of claim 2, wherein an upper end of the rotation strap is secured by a key-hole engagement to the pocket, and an opposed lower end of the rotation strap is secured by a hook-and-loop engagement to the pocket.

4. The orthosis of claim 1, further comprising:
   a cooling pack comprising a reservoir and inlet and outlet tubes extending from a bottom of the reservoir; and
   the cooling pack applied to the pocket such that the inlet and outlet tubes pass through the lower opening of the pocket.

5. The orthosis of claim 1, wherein free ends of the upper straps of the abduction harness are secured by a key-hole engagement to the pocket, and a free end of the lower strap of the abduction harness is secured by a hook-and-loop engagement to the pocket.

6. The orthosis of claim 1, wherein the upper straps of the abduction harness are inelastic and the lower strap of the abduction harness has an elastic portion.

7. The orthosis of claim 1, further comprising an articulating brace extending from the top of the pocket to the bottom of the pocket.

8. An orthosis comprising:
   a waist strap having opposed first and second ends and a lateral portion therebetween, the first and second ends having coupling means for coupling the first and second ends;
   a lower strap having opposed first and second ends and a lateral portion therebetween, the first and second ends of the lower strap having coupling means for coupling the first and second ends of the lower strap;
   a pocket extending between the waist strap and the lower strap, the pocket comprising an inner panel and an outer panel fastened to each other to define an upper opening at a top of the pocket and a lower opening at a bottom of the pocket, the upper opening larger than the lower opening; and
   an abduction harness, for laterally abducting a leg, comprising two upper straps and a lower strap coupled to each other at a central union, wherein the upper straps are secured to the top of the pocket, and the lower strap is secured to the bottom of the pocket.

9. The orthosis of claim 8, further comprising a rotation strap extending from the bottom of the pocket to a location on the waist strap proximate to the top of the pocket.

10. The orthosis of claim 9, wherein an upper end of the rotation strap is secured by a key-hole engagement to the pocket, and an opposed lower end of the rotation strap is secured by a hook-and-loop engagement to the pocket.

11. The orthosis of claim 8, further comprising:
    a cooling pack comprising a reservoir and inlet and outlet tubes extending from a bottom of the reservoir; and
    the cooling pack applied to the pocket such that the inlet and outlet tubes pass through the lower opening of the pocket.

12. The orthosis of claim 8, wherein free ends of the upper straps of the abduction harness are secured by a key-hole engagement to the pocket, and a free end of the lower strap of the abduction harness is secured by a hook-and-loop engagement to the pocket.

13. The orthosis of claim 8, wherein the upper straps of the abduction harness are inelastic and the lower strap of the abduction harness has an elastic portion.

14. The orthosis of claim 8, further comprising an articulating brace extending from the top of the pocket to the bottom of the pocket.

15. An orthosis comprising:
    a waist strap having opposed first and second ends and a lateral portion therebetween, the first and second ends having coupling means for coupling the first and second ends;
    a lower strap having opposed first and second ends and a lateral portion therebetween, the first and second ends of the lower strap having coupling means for coupling the first and second ends of the lower strap;
    a pocket extending between the waist strap and the lower strap, the pocket comprising an inner panel and an outer panel fastened to each other to define an upper opening at a top of the pocket and a lower opening at a bottom of the pocket, the upper opening larger than the lower opening;
    an abduction harness, for laterally abducting a leg, comprising two upper straps and a lower strap coupled to each other at a central union, wherein the upper straps are secured to the top of the pocket, and the lower strap is secured to the bottom of the pocket; and
    a rotation strap extending from the bottom of the pocket to a location on the waist strap proximate to the top of the pocket.

16. The orthosis of claim 15, further comprising:
    a cooling pack comprising a reservoir and inlet and outlet tubes extending from a bottom of the reservoir; and
    the cooling pack applied to the pocket such that the inlet and outlet tubes pass through the lower opening of the pocket.

17. The orthosis of claim 15, wherein the top of the pocket is secured to the lateral portion of the waist strap, and the first and second ends of the lower strap are secured on the bottom of the pocket.

18. The orthosis of claim 15, further comprising an articulating brace extending from the top of the pocket to the bottom of the pocket.

19. The orthosis of claim 15, wherein free ends of the upper straps of the abduction harness are secured by a key-hole engagement to the pocket, and a free end of the lower strap of the abduction harness is secured in a hook-and-loop engagement to the pocket.

20. The orthosis of claim 15, wherein the upper straps of the abduction harness are inelastic and the lower strap of the abduction harness has an elastic portion.

21. The orthosis of claim 15, wherein an upper end of the rotation strap is secured by a key-hole engagement to the pocket, and an opposed lower end of the rotation strap is secured by a hook-and-loop engagement to the pocket.

* * * * *